US008954472B1

(12) United States Patent
Chapman et al.

(10) Patent No.: US 8,954,472 B1
(45) Date of Patent: Feb. 10, 2015

(54) METHOD AND SYSTEM FOR COLLECTING, STORING AND ANALYZING CLINICAL AND RADIOLOGIC DATA

(75) Inventors: M. Weston Chapman, Hanover, NH (US); Steven Maker, Lyme, NH (US); Samuel B. Kadson, West Roxbury, MA (US)

(73) Assignee: M2S, Inc., West Lebanon, NH (US)

( * ) Notice: Subject to any disclaimer, the term of this patent is extended or adjusted under 35 U.S.C. 154(b) by 36 days.

(21) Appl. No.: 12/965,450

(22) Filed: Dec. 10, 2010
(Under 37 CFR 1.47)

Related U.S. Application Data

(60) Provisional application No. 61/283,918, filed on Dec. 10, 2009.

(51) Int. Cl.
*G06F 17/30* (2006.01)

(52) U.S. Cl.
USPC .......................... 707/785; 707/769; 719/315

(58) Field of Classification Search
USPC ......................................... 707/785; 719/315
See application file for complete search history.

(56) References Cited

U.S. PATENT DOCUMENTS

2004/0034550 A1* 2/2004 Menschik et al. ................ 705/3
2011/0258000 A1* 10/2011 Green et al. ..................... 705/3

* cited by examiner

*Primary Examiner* — Belix M Ortiz Ditren
(74) *Attorney, Agent, or Firm* — Choate, Hall & Stewart LLP; William R. Haulbrook

(57) ABSTRACT

The invention relates to an online web-based medical database and collaboration tool that can be used by surgeons, hospitals, medical institutions, manufacturers and others to collect, store, analyze and harvest clinical and radiologic data. The clinical registry system includes a registry database and a registry processor in electrical communication with the registry database and performing operations on the registry database. The registry database stores patient data from a plurality of sites, a plurality of registry groups and an indicator for each of the plurality of sites identifying which of the plurality of registry groups each site is a member. The members of a registry group have access to aggregated data and comparative reports of all the registry group members in real-time. Each site may be a member of one registry group, multiple registry groups, or no registry groups.

14 Claims, 11 Drawing Sheets

METHOD AND SYSTEM FOR COLLECTING, STORING AND ANALYZING CLINICAL AND RADIOLOGIC DATA

CROSS-REFERENCE TO RELATED APPLICATIONS

This application claims priority to U.S. provisional application Ser. No. 61/283,918 entitled, "Clinical data pathways", filed on Dec. 10, 2010, the entire contents of which are hereby incorporated by reference.

STATEMENT REGARDING FEDERALLY SPONSORED RESEARCH OR DEVELOPMENT

Not applicable.

REFERENCE TO A SEQUENCE LISTING, A TABLE, OR COMPUTER PROGRAM LISTING COMPACT DISC APPENDIX

Not applicable.

BACKGROUND OF THE INVENTION

The invention relates generally to online medical databases, and more specifically to an online medical database and collaboration tool that can be used by surgeons, hospitals, medical institutions, manufacturers and others to collect, store, analyze and harvest clinical and radiologic data.

Currently hospitals and other medical institutions have medical databases that can store patient identification information and medical information. However, many of these database systems are proprietary to the particular medical institution and cannot communicate with the database systems of other medical institutions. In addition, many of these systems may only be used to retrieve data regarding a particular patient.

BRIEF SUMMARY OF THE INVENTION

The invention relates generally to a method and system for collecting, storing, and analyzing clinical and radiologic data. The system includes a database storing patient data from a plurality of sites and a registry processor. Each of the plurality of sites may store their data segregated from the remainder of the sites, or may "pool" their data with other sites. Each group of sites pooling data is termed a "registry group". A site may belong to one, a plurality, or no registry groups.

One object of the invention is to provide a clinical data registry that provides real-time data access to patient data for clinicians, hospitals, etc. Another object of the invention is to allow different medical providers to share clinical and/or aggregated data so that they may evaluate the efficacy of different treatment protocols, how well a particular medical institution is doing as compared to others, the recovery rate of patients of a particular surgeon, etc. These comparisons provide medical institutions with information regarding the areas in which they are doing well, and the ability to recognize where they need improvement. This data is useful in order to improve the quality of patient care.

Yet another object of the invention is to provide a clinical data registry that provides users the ability to customize data fields so that the users still feel that they have "control" of their data. Still another object of the invention is to provide a clinical data registry that provides users the ability to generate and run customized queries on the data.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

FIG. 3 is a pictorial view of screenshot of an embodiment of a patient information screen displayed to a user;

FIG. 6 is a pictorial view of an embodiment of a screenshot presented to create a user and assign privileges to that user;

FIG. 7 is a pictorial view of an embodiment of a screenshot showing an example output of an embodiment of an ad hoc report generation module;

Like reference characters in the respective drawn figures indicate corresponding parts.

DETAILED DESCRIPTION OF THE INVENTION

Figure 1:
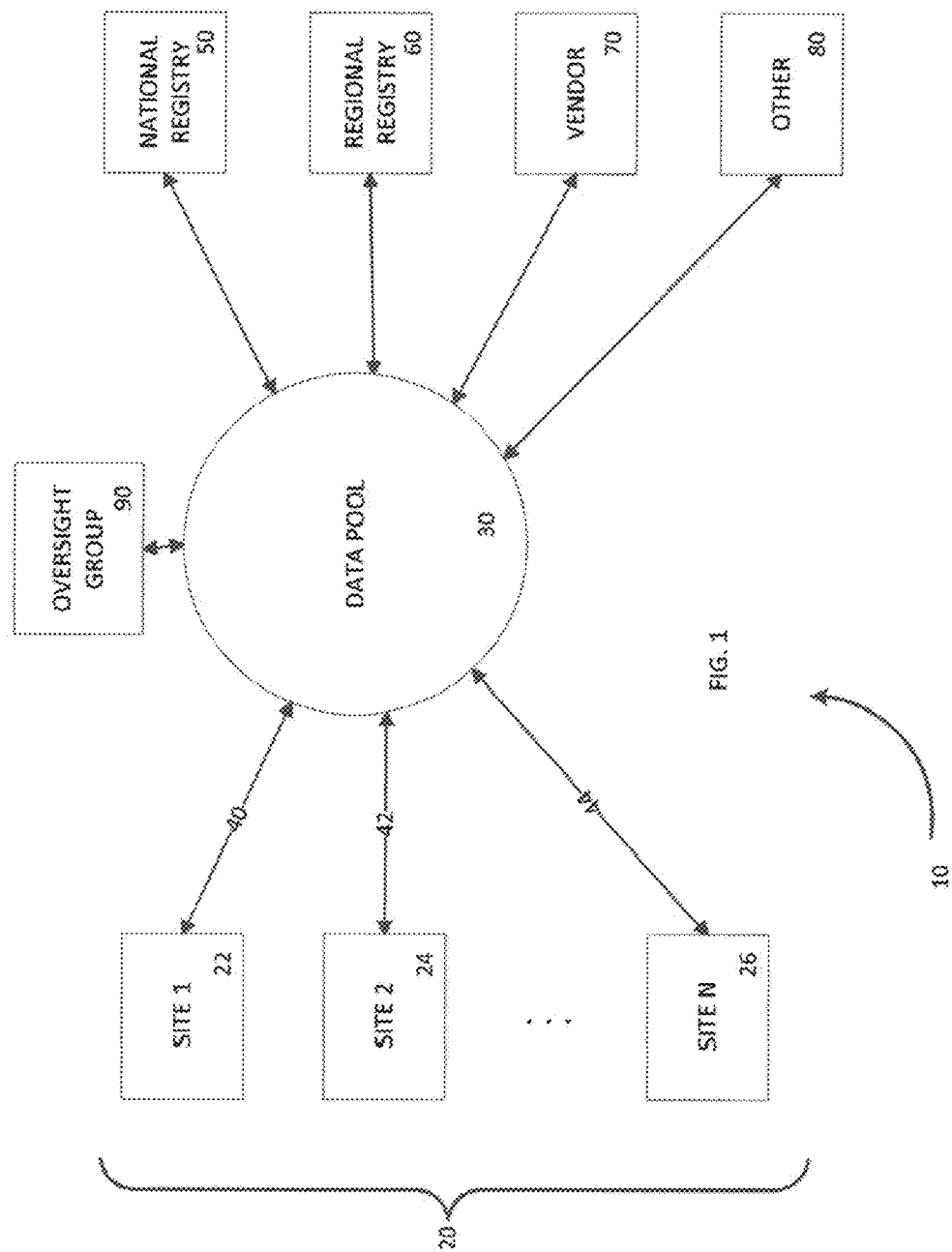
FIG. 1 is a block diagram of an embodiment of a system for collecting, storing, analyzing and sharing clinical and radiologic data.

Referring to FIG. 1 and in brief overview, an embodiment of a clinical data registry system 10 for collecting, storing, analyzing and sharing clinical and radiologic data constructed in accordance with the invention includes a plurality of data sites 20 (site$_1$ 22, site$_2$ 24 through site$_N$ 26) and a data pool 30. The plurality of data sites 20 may be hospitals, research facilities, doctors' offices, universities, insurance companies, medical or pharmaceutical companies or any other type of institution that stores data about patients. The plurality of sites 20 may also be referred to herein as "institutions", but the sites may be any of the types of entities listed above. Each site 20 collects patient data using protocol specifications. The protocol specifications may be any specifications for the data to be collected, so long as the plurality of sites 20 use the same protocol specifications. The protocol specifies how and when data is combined and how the data is reported. The patient data may be stored by the individual sites 22, 24, 26 and/or contributed to and stored in the data pool 30. Each site 20 may have its own patient registry that is stored separately in the data pool 30. In one embodiment, the sites 20 may each develop customized data pools; however the data is still collected according to the protocol specifications.

In the embodiment shown, the plurality of sites 20 and the data pool 30 are connected via communications links 40, 42, 44. The communications links 40, 42, 44 may be any type of communication systems by which the plurality of sites 20 and the data pool 30 may communicate. For example, the plurality of sites 20 and the data pool 30 may communicate by a global communications network (i.e. Internet or World Wide Web), or via an intranet. In yet another embodiment the plurality of sites 20 may communicate with the data pool 30 using different types of communication systems. In still another embodiment, the plurality of sites 20 and the data pool 30 are parts of the same computer. That is, the same computer may be used to access and query the database (data pool 30) as well as store the information.

The data pool 30 may include a single clinical data registry or multiple data registries. The data registries may be for the same medical condition or for different medical conditions. For example, there may be a vascular registry, an oncology registry, etc. All of the registries are created using a common platform. The common platform allows users real-time access to their own data, and enables users to pool their data together as desired. In one embodiment, the data pool 30 is maintained in a relational database having specified defined data fields. The data pool 30 is sorted according to protocol via site-specified front ends. The sites 20 may define the fields, reports, participants and other parameters. The centralized data pool 30 also allows for communication between different sites 20.

In another embodiment, the system 10 optionally includes other entities to which data may be exported from the data pool 30 or imported to the data pool 30. For example, the system 10 may include a national registry 50, a regional registry 60, vendor sites 70 or other types of entities 80 that may wish to utilize or contribute to data stored in the data pool 30.

In yet another embodiment, the system 10 may include an oversight group 90. An example of an oversight group 90 is a patient safety organization. The purpose of a patient safety organization is to enable surgeons to pool their data in an effort to improve patient care without the threat of the comparative reports being legally discoverable.

Figure 2:
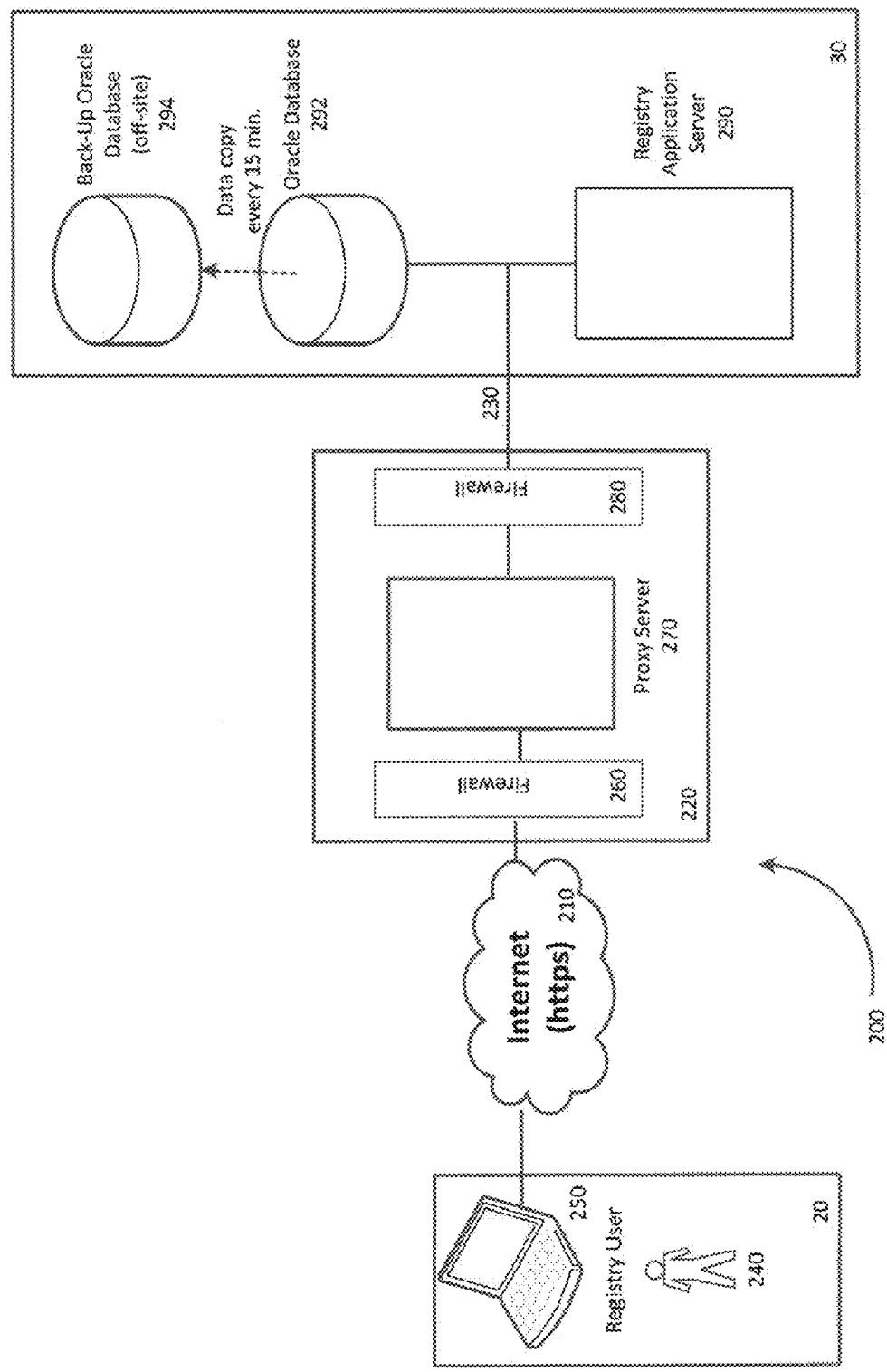
FIG. 2 is block diagram of an embodiment of a clinical data registry according to the invention.

An embodiment 200 of the system 10 is shown in greater detail in FIG. 2. The embodiment 200 of the system 10 shown in FIG. 2 is simplified to include only one site 20 communicating with the data pool 30. The system embodiment 200 includes a site 20, a first communications link 210, data security elements 220, a second communications link 230, and the data pool 30. At the site 20, a user 240 utilizes a client computer 250 to communicate with the data pool 30. The client computer 250 may be any computer or other device that is capable of executing a web browser. There is no application-specific software required on the client computer. In other embodiments, the client computer 250 may also be capable of executing other applications, such as word processing, spreadsheet and email applications. The user 240 uses the web browser on the client computer 250 to access a website hosted by the data pool 30. The terms user, customer, clinician, surgeon, etc. when used in connection with reference number 240 all mean the individual entering the patient or other data to be sent to the data pool 30. The client computer 250 may be a computer located at the site 20, or may be any other computer that has a web browser and is connected to the Internet. As the data pool 30 is web-based, surgeons or medical institutions can access the data pool 30 from any physical location.

In the embodiment shown in FIG. 2, the communications link 210 used by the client computer 250 to communicate with the data pool 30 is the Internet and the protocol used is a security protocol such as SSL. To increase the security of the system 200, the security elements 220 are used. In the embodiment shown, the security elements 220 include a first firewall 260, a proxy server 270 and a second firewall 280. In other embodiments, other combinations of security elements that are well known in the art may be used.

The data pool 30 includes a registry processor 290, a primary database 292 and a backup database 294. The processor 290 may also be referred to herein as a registry application server. The processor 290 receives information or commands from the client computer 250 (through the communications link 210 and security elements 220) and performs operations on the data stored in the primary database 292. In one embodiment, the primary database 292 and the backup database 294 are relational databases, storing information in tables. In other embodiments, the primary database 292 and the backup database 294 are object-oriented databases or any other form of database capable of storing data. In one embodiment in which a relational database is used, the primary database 292 includes two tables. The first table is a patient information table and stores records for patient information such as the patient's personal information such as name, address, date of birth, social security number, and other personal identification information. The first table may also store information relating to the patient's medical conditions. The second table is a procedure table and stores records relating to medical procedures performed, such as type of procedure, pre-operative information, post-operative information, different stages of a procedure or protocol, etc.

The data stored in the primary database 292 is copied into the backup database 294 to help ensure that no data is lost should the primary database 292 be compromised. The backup database 294 may be at the same or different location than the primary database 292. The data in the primary database 292 may be backed-up to the backup database 294 at regular intervals or at the direction of a database administrator.

As described above, the system 200 is a web-based system for data collection and analysis. A user 240 may add information or perform operations on an existing registry, create a new registry, and combine clinical data from multiple existing registries. The ability to combine clinical data from multiple existing registries is due to the registries being developed on a common platform. In one embodiment, different institutions or entities may be grouped together into registry groups based on common interests or geographical location. For example, two hospitals that specialize in treating vascular conditions may be grouped into a vascular registry group so that they may share data. Similarly, two hospitals that are in geographic proximity to each other may be grouped into a regional registry group so that they may share data. In one embodiment having registry groups, data sharing is dictated by the entities included in the group. Members of a registry group may agree to use a common format to enter and view data. However, in one embodiment, the individual members of a registry group have the flexibility to add custom fields to their databases in addition to the fields that are common to all the members of the registry group. For example, one member of the registry group may want to track financial data relating to a specific procedure whereas other members are not interested in collecting that data. This custom field may be presented to or kept confidential from the other members of the group. In another embodiment, when data is shared between multiple members that use different data formats, a matching algorithm may be used to identify the fields that they share and aggregate the information. Correlations can be made between data spread across registries serving disparate fields of medicine, such as oncology and cardio-vascular diseases. The cross-correlation between registries may help form causal relationships that could not be identified by the analysis of each set of data individually.

Figure 3:
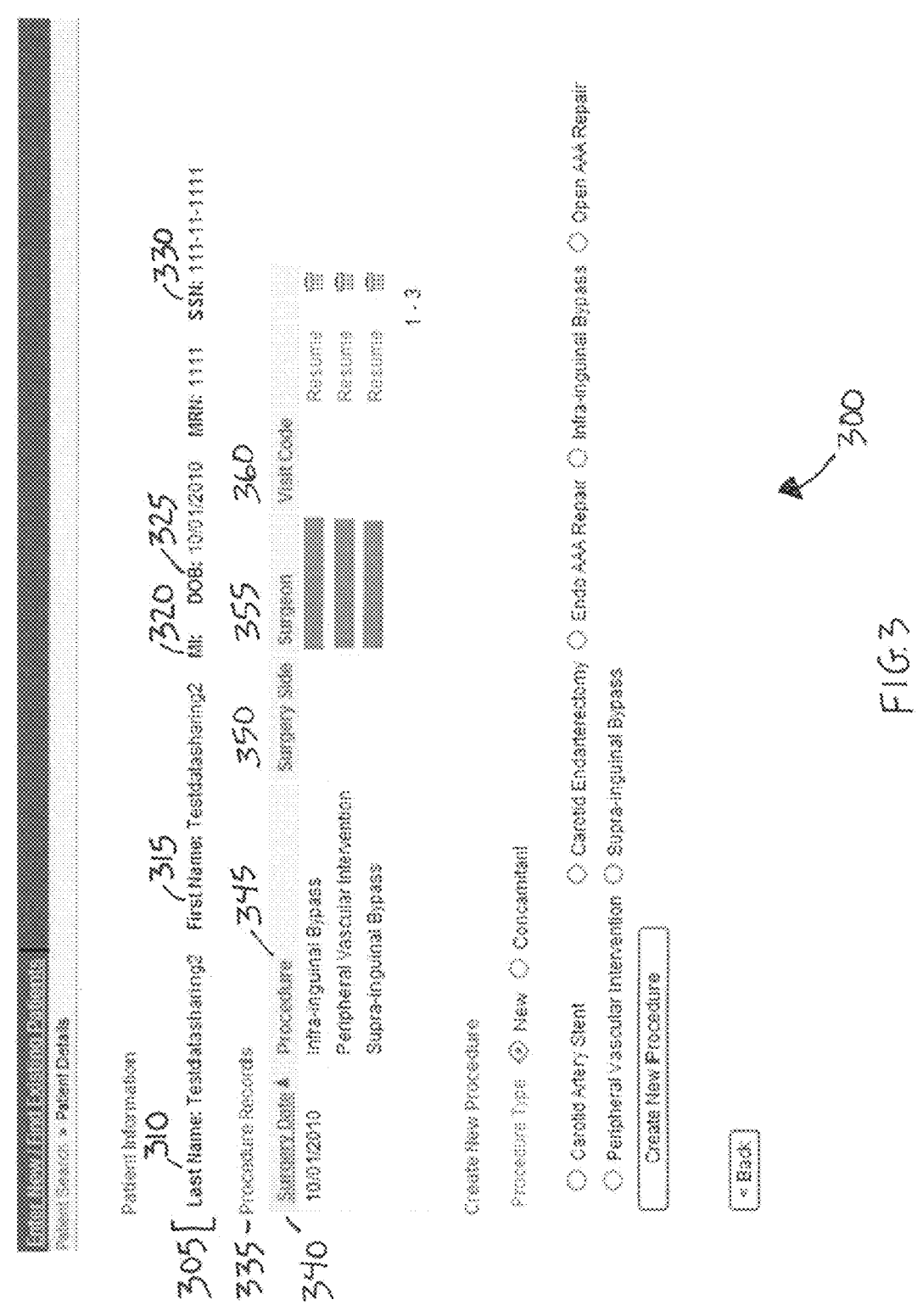

FIG. 3 shows an example screenshot 300 of a patient information screen that may be displayed to a user. In this example, the members of the registry group have decided upon certain common patient information fields 305, such as patient last name 310, patient first name 315, middle initial 320, date of birth 325, and social security number 330. The patient information screen 300 also includes procedure records 335 for the patient. In the example shown, the patient named "Testdatasharing2" had surgery on Oct. 1, 2010 consisting of three medical procedures. The procedure records 335 for the patient include fields for procedure date 340, procedure name 345, surgery side 350, surgeon 355, and visit code 360. A user may add an additional procedure for a patient by accessing the patient's record and selecting the "create new procedure" command. The user is then prompted to enter information for the different procedure record fields described above.

Figure 4:
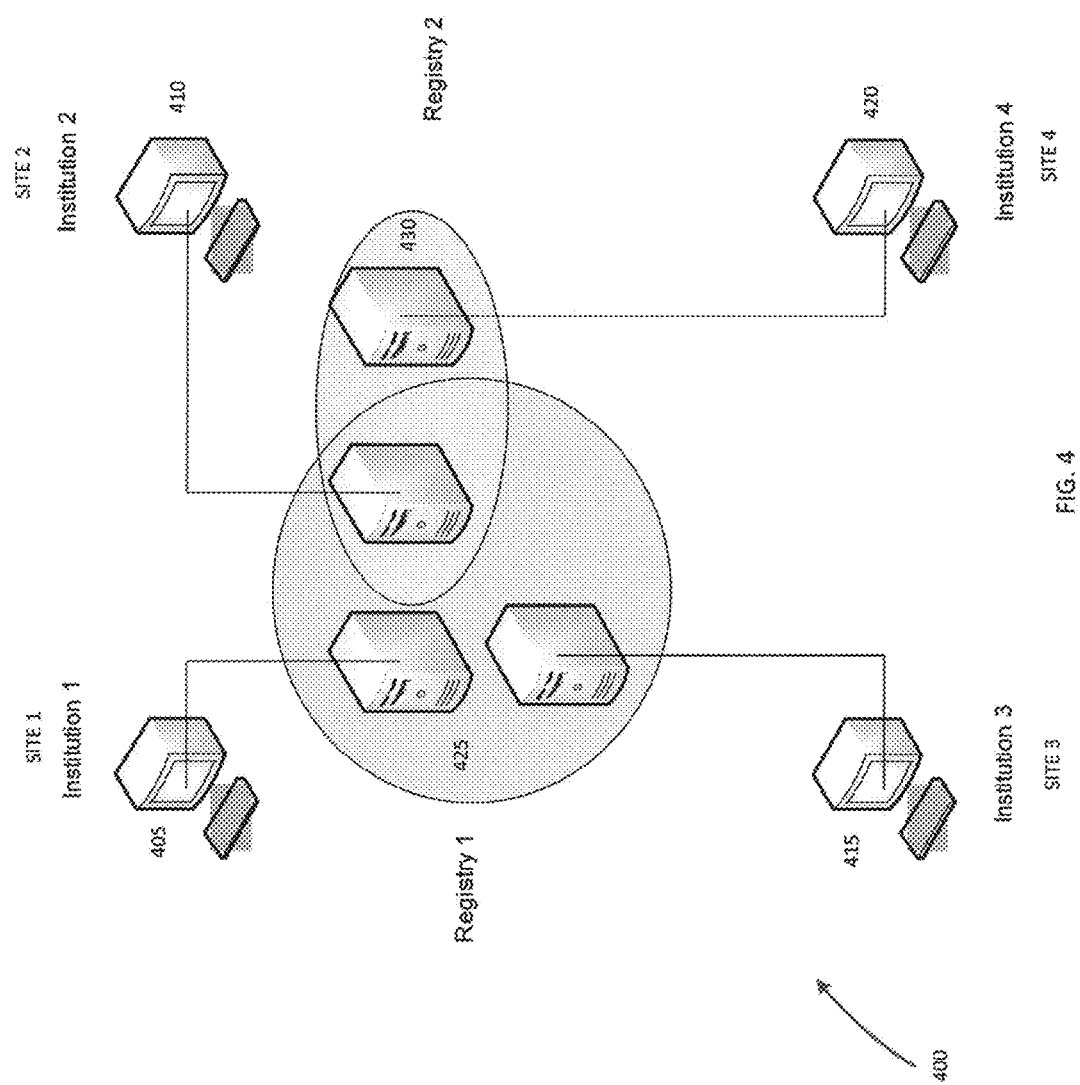
FIG. 4 is a block diagram of an embodiment of a clinical data registry that allows users to pool their data within designated registry groups for analysis.

As described above, multiple entities storing data within the data pool 30 may be grouped into registry groups and share data with each other. FIG. 4 is a block diagram of an embodiment of a system 400 that allows users to pool their data within designated groups for analysis. In the registry system 400 shown in FIG. 4, there are four sites, or institutions that store data in the registry system 400—site$_1$ 405, site$_2$ 410, site$_3$ 415 and site$_4$ 420. In this particular example, the sites are different medical institutions. As explained above, the sites may be any entities or individuals that store and analyze clinical data. There are two registry groups, Registry1 425 and Registry2 430. The first group Registry1 425 includes data from site$_1$ 405, site$_2$ 410 and site$_3$ 415. The second group Registry2 430 includes data from site$_2$ 410 and site$_4$ 420. As shown in the example of FIG. 4, sites may be included in more than one registry group. This allows institutions choosing to pool their data with a specific group of hospitals at the same time to pool their data with a separate group of hospitals. There may be many layers of overlap between the registry groups. The data entered by each of the sites is available to generate aggregated data or comparative reports for registry group members on a real-time basis. However, in one embodiment, the raw clinical data itself is only available to the center that entered the data, but not to any other registry group members.

Data entered into the clinical registry system is owned by the site/institution to which it is associated. Each institution specifies the data they plan to collect and with whom they want to pool data. Data entered into the system can be downloaded at any time by an institution. Records in are stored in a form where it is easy to associate and dissociate institutions and groups of institutions without compromising the integrity of data. For example, if an institution which was a part of a regional quality improvement group wished to withdraw, its data could be selectively removed from the data pool without affecting the integrity of the rest of the data.

One benefit of institutions pooling their data into registry groups is that the institutions may benchmark their results against each other. The flexibility of the registry system 400 enables a form of data harvesting that is unique from previously existing clinical registries. Data collected on multiple medical conditions may be pooled and analyzed to establish relationships between medical conditions. In addition, institutions collecting data on multiple medical conditions may reduce the data entry burden as data elements common to both medical conditions (e.g. anesthesia, diabetes status, blood pressure, antibiotic usage) may be shared without requiring redundant data entry.

Figure 5:
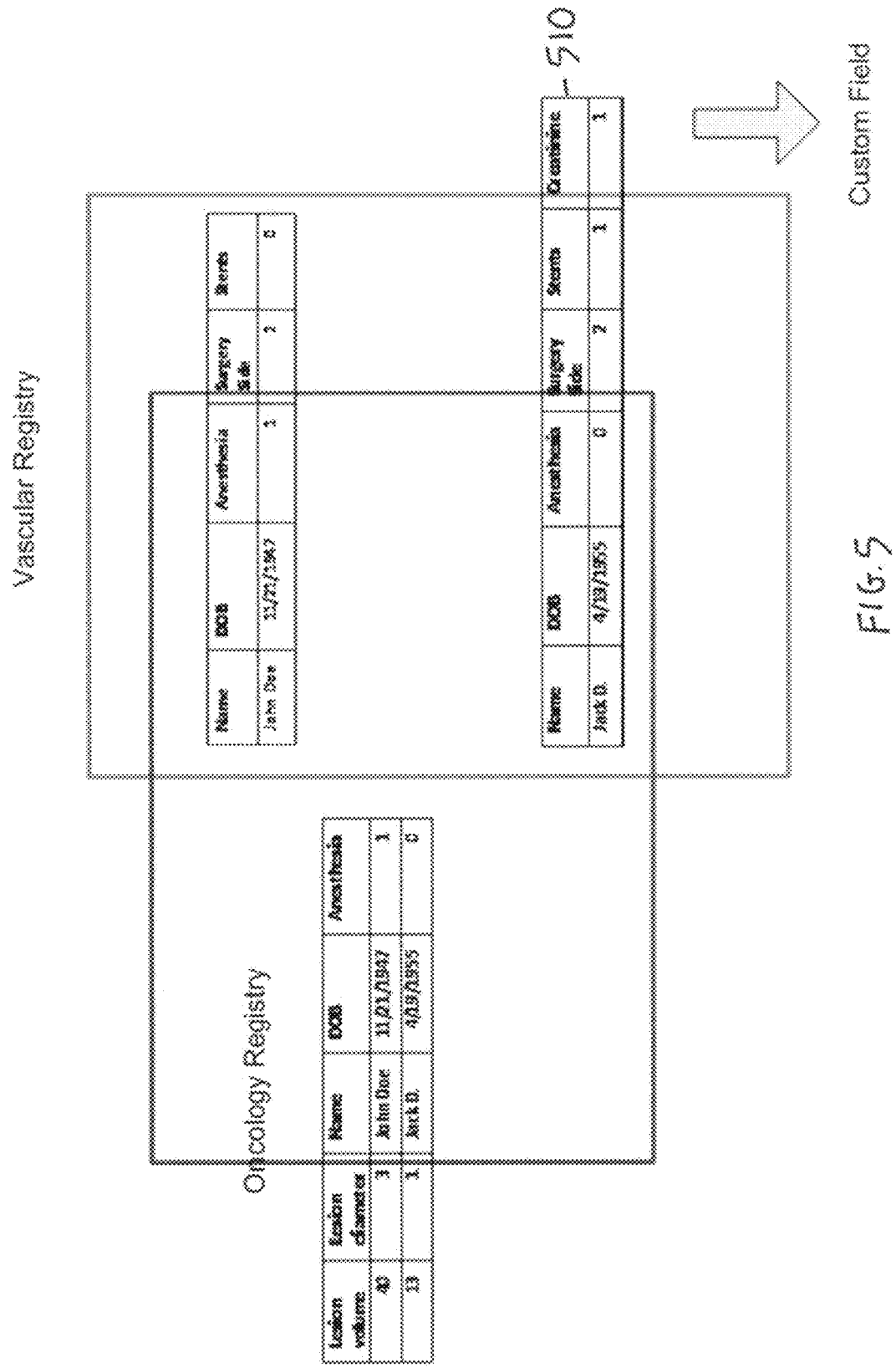
FIG. 5 is a pictorial view of data records of an embodiment of a clinical data registry that allows users share data elements related to a single patient between different registries.

FIG. 5 shows an example of patient data that has data elements common to multiple medical conditions. For example, patients John Doe and Jack D. have their names, dates of birth and anesthesia information stored in the Oncology Registry and the Vascular Registry. As described above, in one embodiment, institutions do not have restrictions on the number of fields into which they can enter data.

Another benefit of the registry system according to the invention is that it allows institutions and surgeons to longitudinally track individual patient data in real-time as it is entered, or view aggregate reports seamlessly. Procedures are associated with specific patient records and as well as surgeons. Patient records and surgeons are associated with institutions. Surgeons practicing at multiple hospitals can enter and view procedures and aggregate reports for multiple institutions using the same username and password combination. Data collected in this format can also link patients between institutions for improved longitudinal tracking of patient outcomes.

While the data within specific registry groups is standardized, participating institutions can choose to support additional fields, known as customizable fields, which they use for internal purposes or for data sharing with researchers or other institutions. Referring again to FIG. 5, an example is the custom field 510. In one embodiment, the registry system allows the users with appropriate privileges to create and edit customized form sections and fields that are only visible to the users in a particular institution/hospital or in a specific group of institutions/hospitals. When creating their own customized fields for data collection, the users can choose free text, drop down, numeric value, date picker, checkbox, and radio group fields that have been built into the procedure forms. After the creation of the customized field, it is instantly available to the targeted users for data collection. Data collected in customized fields is available for analysis in the ad-hoc reports, instant download and printing.

In another embodiment of the registry system, users with appropriate privileges may design a workflow for a specific site for data entry. The user who completes his/her portion of work can assign the rest of the work to another user. After the assignment, the work will automatically appear on the assignee's work list and at the same time an email notification will be sent to the assignee.

In still another embodiment of the clinical data registry, radiographic images and image measurements are integrated into the clinical data records. This feature provides a uniquely comprehensive outcomes analysis tool. Users can upload pre-operative and post-operative 2-D and 3-D images directly into clinical data registry for web-based viewing and analysis. Images are associated with patients and their clinical data. Pre-operative and post-operative images can be easily compared side-by-side for improved outcomes tracking at the individual patient-level. Measurements from these images and changes in measurements across time are populated into the clinical data and may be made available for comparative reporting as directed by the institution. Analysis of potential associations between risk factors and patient outcomes are made easier through using a single data repository for both clinical and radiologic data.

As described briefly above, embodiments of the clinical data registry may include a privilege assignment module that assigns privileges to different types of users. Roles may be associated with specific innate permissions but may also be customized by each institution to meet their specific requirements. For example, assigning the role of surgeon indicates that the user should be added to a specific drop down menu; this innate permission is the same at all institutions. Nevertheless, a user with the role of surgeon may have different access to patient data dependent upon the institution. The adaptability of the permission module allows institutions to customize their users' access to the data maintained in and available through the clinical data registry.

Figure 6:
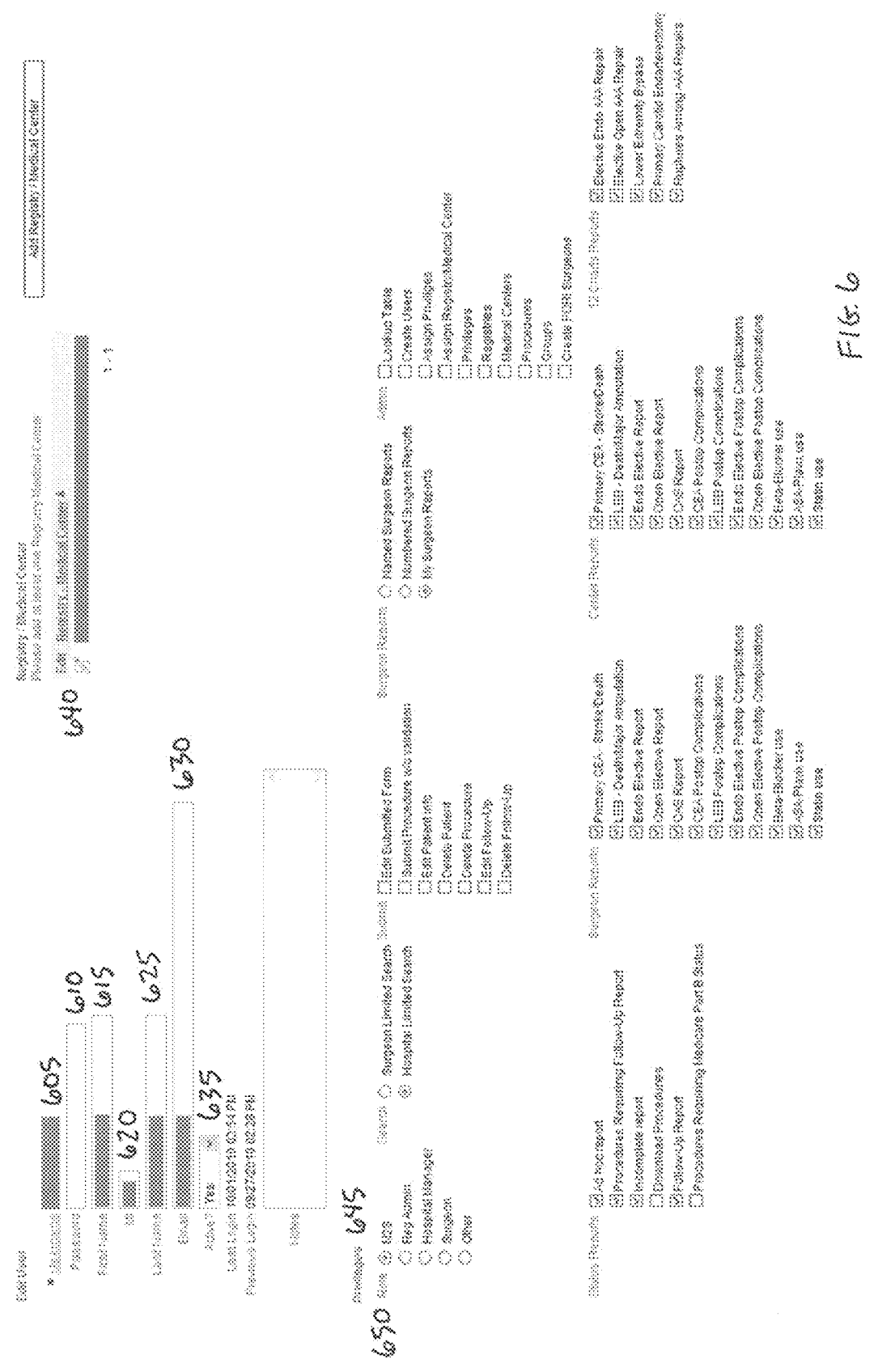

FIG. 6 shows an embodiment of a screenshot of a data entry page used to create a user and assign privileges to that user. The page includes fields for username 605, password 610, first name 615, middle initial 620, last name 625, email address 630, status 635 (active/inactive), registry groups to which the user belongs 640, and the privileges 645 that the user has. The user may be assigned a role 650, such as administrator, hospital manager, surgeon, etc., and may be granted different privileges.

Figure 7:
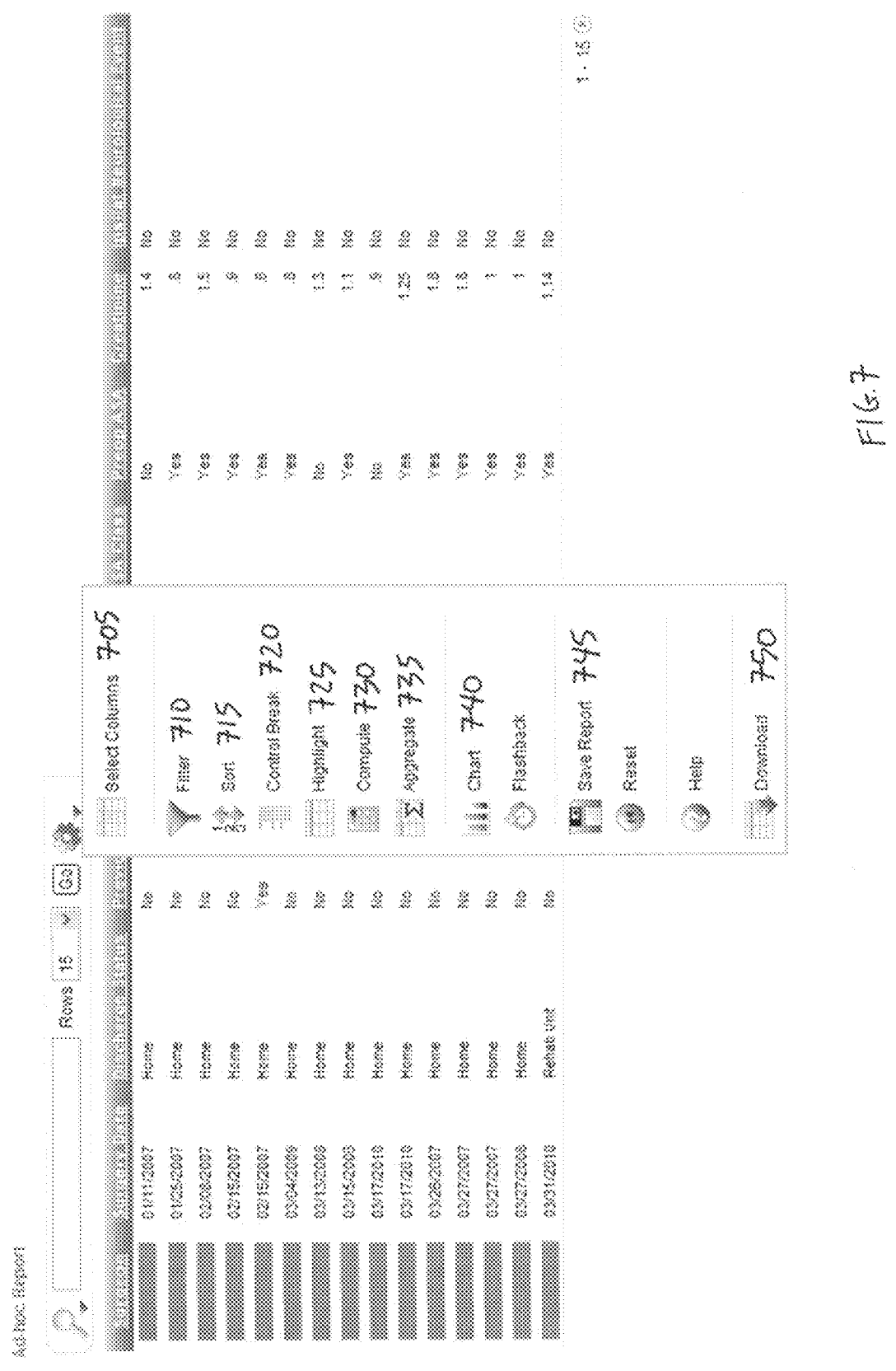

Data entered into the clinical registry system is made available to the institutions in real-time for the purpose of ad hoc reporting. The ad hoc reporting feature allows users to build their own queries for the purpose of investigating trends appearing in their own data. As shown in FIG. 7, this feature allows users to select columns 705, create filters 710, change the sort order 715, add controlled breaks 720, highlight rows/columns/cells 725, create computations 730, create aggregations 735, plot analysis result in charts 740, save report settings 745 and download data 750 for further analysis.

Users may choose a subset of data fields of interest or all fields with which to work. The ad hoc feature allows users to apply multiple filters 710 to the data to view possible associations between data fields. These associations may be presented in a number of different chart formats and all graphs may be saved for future reference. Data may also be presented in a tabular report. In this format, a surgeon can see how he/she performs on a specific measure as compared with an average of other surgeons participating in the same group or a hospital can see how it compares against the average of other participating hospitals.

Identified data is made available to the institution with which it is associated in the ad hoc reporting feature. For institutions choosing to pool data with other institutions, de-identified data from all the participating institutions is made available for ad hoc reporting. The purpose of the ad hoc reports is to identify possible trends emerging from the data that are worthy of further statistical analysis.

For institutions choosing to pool data with other institutions, the clinical data registry makes possible the generation of comparative data reports in real time. Through the set-up of the institutions in the database, the data from institutions choosing to share data becomes available for inclusion in reports as soon as it is entered as a completed record into the database. When a user from one of the registry groups enters a query to obtain a comparative report, the database analyzes all of the pooled data and then creates a comparative or benchmarked report which instantly appears on the user's computer screen. One embodiment of the clinical data registry includes a number of standard queries that are designed to permit users to generate benchmarked reports based on data entered into the system in real-time. Benchmarked reports provide real-time feedback to surgeons and centers as they allow surgeons and centers to compare their performance with that of a defined group of peers (registry group) on pre-determined quality measures.

Figure 8:
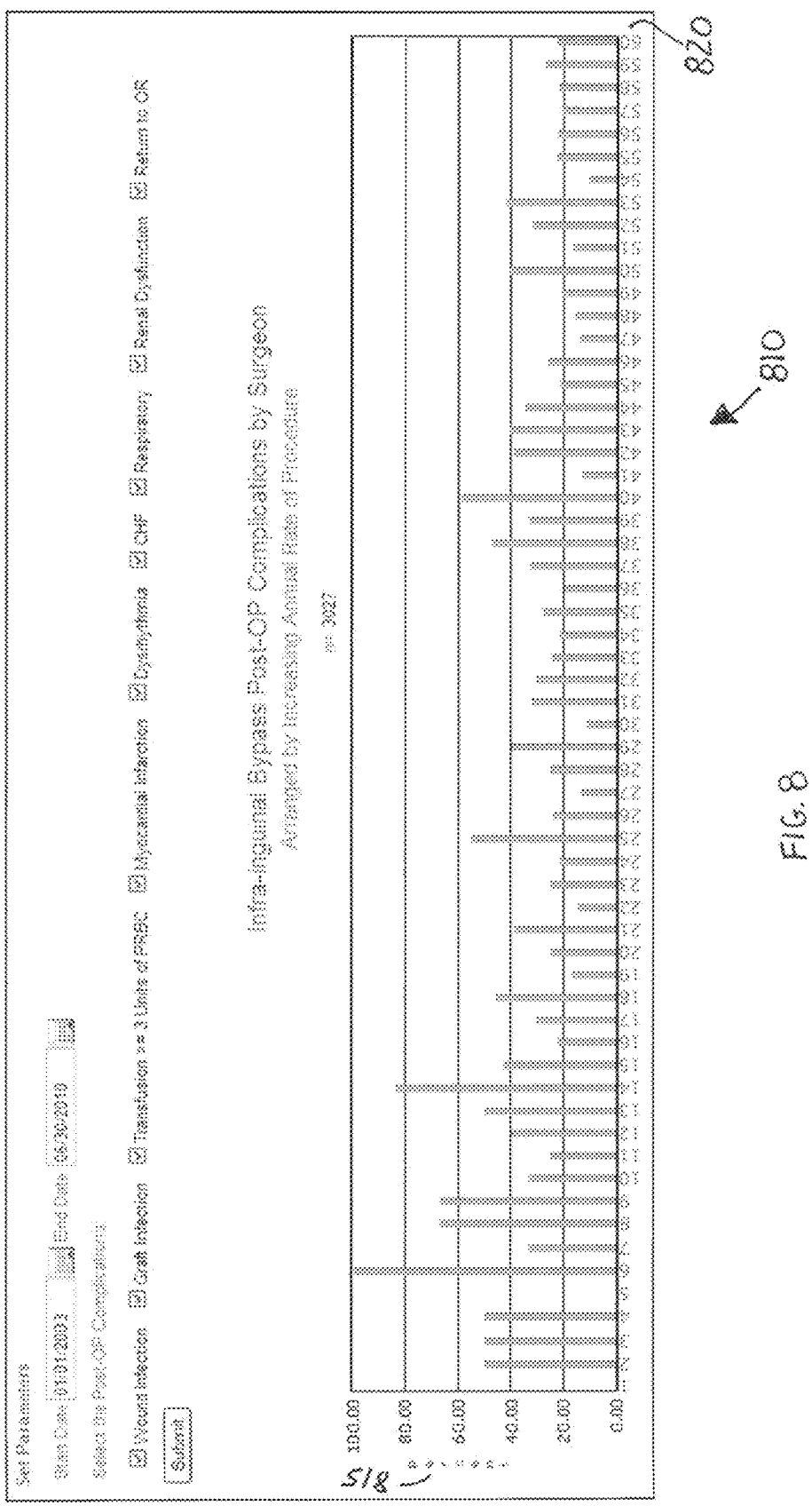
FIG. 8 is a pictorial view of a graph of percent complications as a function of the surgeon performing the procedure.
Figure 9:
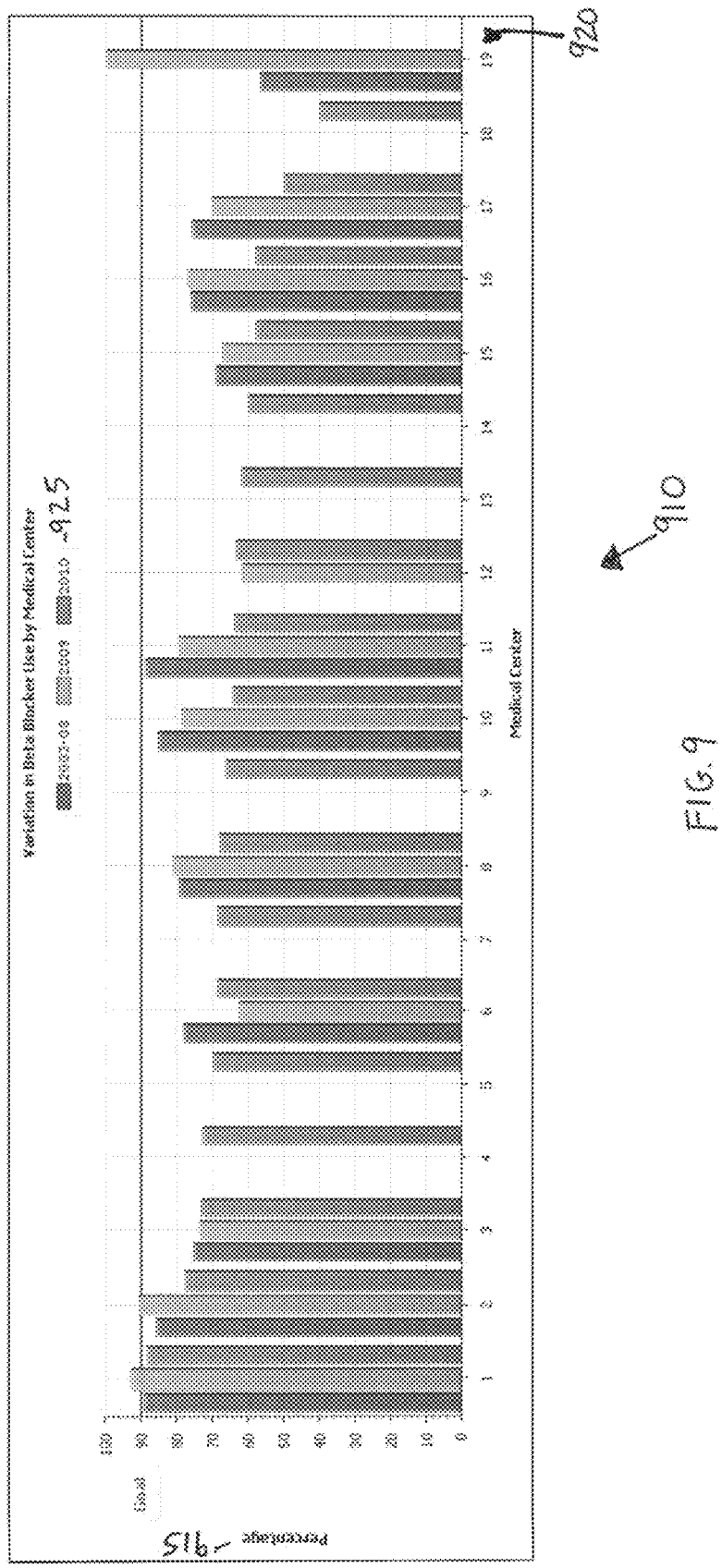
FIG. 9 is pictorial view of a graph of percentage of beta blocker use as a function of medical center.

FIG. 8 is an example of a benchmark report on the surgeon level and FIG. 9 is an example of a benchmark report on a center-level. The graph 810 of FIG. 8 plots percent complications 815 as a function of the surgeon 820 performing the procedure shown. Each of the numbers in the x-axis represents a different surgeon. For example, the surgeon assigned number 12 has approximately a 40 percent patient complication rate. If the user is a surgeon, he/she will be able to identify himself/herself by their annualized rate of procedure rank. As this number is dynamic and changes depending on the annual procedure volume of the surgeons, it maintains physicians' anonymity but allows them to benchmark against other individuals at their institution. Depending on the report privilege the user is given, the report may be blinded differently.

The graph 910 of FIG. 9 plots percent use of beta blocker 915 as a function of medical center 920 and year 925. For example, the medical center assigned number 11, had approximately an 88% use of beta blockers in 2003-2008, an 80% use of beta blockers in 2009 and a 65% use of beta blockers in 2010. In one embodiment of the clinical data registry, the user will only see the initials of the center name that he/she is associated with when running the report. One user can be associated with multiple centers, but he/she will be forced to choose one center before the report can run. So, the initials displayed on the report should only be the one of the center that the user chooses before running the report.

Figure 10:
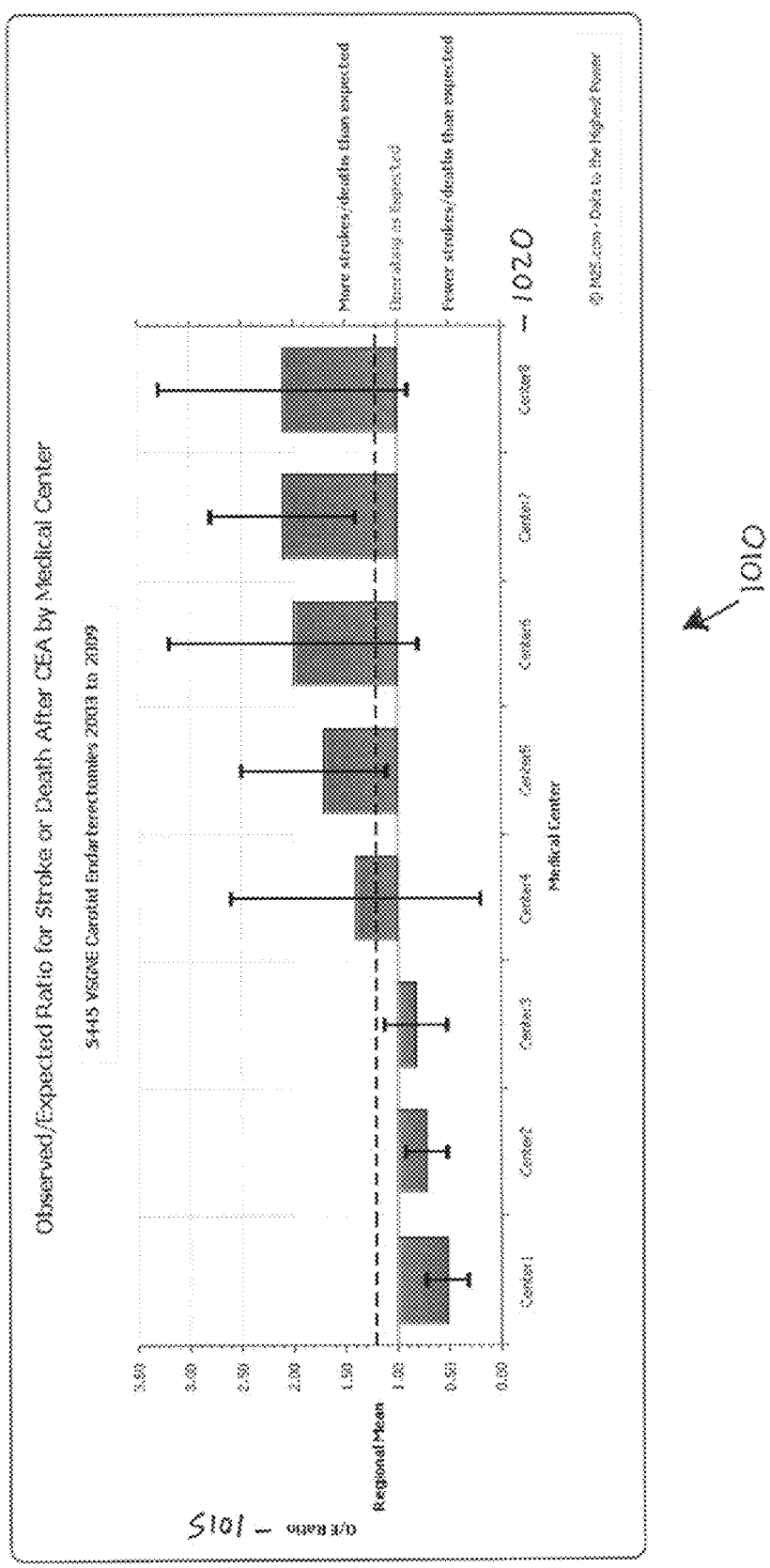
FIG. 10 is a pictorial view of a screenshot showing a graph of the observed/expected ratio for stroke or death after CEA as a function of medical center.

For institutions choosing to pool data with other institutions and join a registry group, the clinical data registry also makes possible the tracking of a center's performance against that of a chosen group of institutions over time. Often, the chosen group of institutions is a regional group that is institutions located in the same geographic region. These reports show how a center compares to the Regional Group on several pre-determined quality metrics over a specified period of time. These quality metrics are established by the Regional Group as being important determinants of the quality of patient care and/or patient outcomes. Regional Groups may also set goals for performance of specific quality metrics which can be displayed on the report. Tracking of an individual center's performance as well as a Regional Group's performance on a specific quality metric can be used to demonstrate changes in clinical practice which may be analyzed for associations with changes in patient outcomes. As an example, the graph 1010 of FIG. 10 plots the observed/expected ratio for stroke or death after CEA 1015 as a function of medical center 1020.

In one embodiment the clinical data registry is able to integrate with existing hospital database systems. In this embodiment, the clinical data registry system is able to communicate with the hospital system and extract data from the hospital system. This data is then analyzed, validated, and added to the registry. For example, a hospital may use multiple data collection terminals. Patients enter their details at a patient terminal before operations are performed on them. The hospital secretary adds additional pre-operative information to the patient form and it is stored on that workstation. Within the operating room, a separate feed keeps track of the patient's vital signs and automatically uploads it to a data repository. The surgeon adds additional information to the form such as measurements, heart rate and complications. This information is combined and stored at the OR terminal. Towards the end of the procedure, billing and documentation information is stored on a workstation that's physically separated from the previous two terminals. The data from all of these terminals may be imported into the clinical data registry system. In one such embodiment, this data is passed through multiple levels of constraint checks and reorganized to obtain usable data that can be inserted into the database and used to generate reports.

Figure 11:
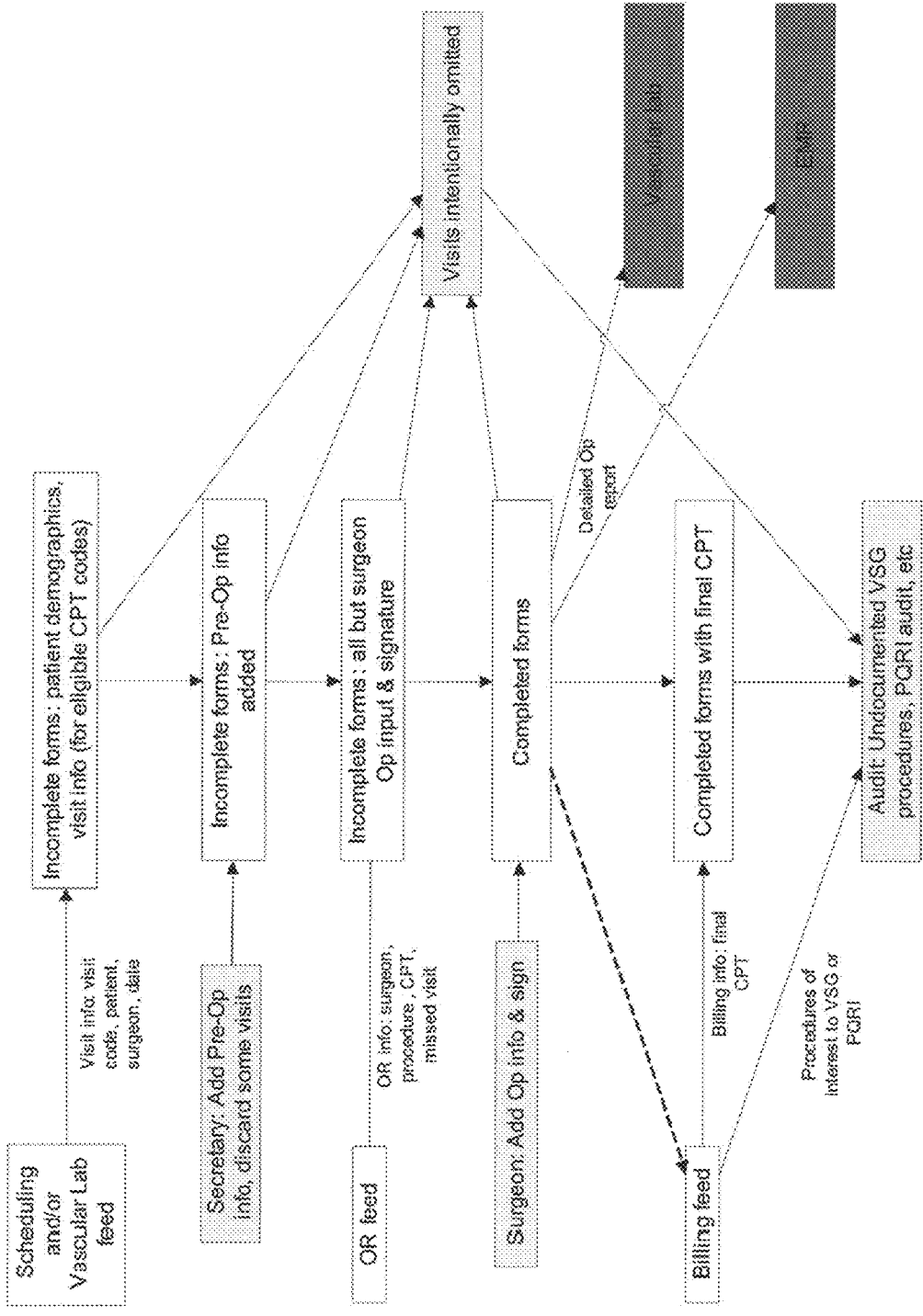
FIG. 11 is a flowchart representation of an embodiment of a process for importing patient data from a hospital electronic medical record ("EMR") system into an embodiment of the clinical data registry.

FIG. 11 is a flowchart representation of an embodiment of a process for importing patient data from a hospital system into an embodiment of the clinical data registry. The clinical data registry has the ability to integrate with external hospital EMR systems and automatically pull data from them. By integrating with EMR systems, there can be a bi-directional data flow to and from the clinical data registry database. This reduces the need for hospital data entry clerks to reenter the same data multiple times at different locations in the database. Also, it eliminates problems of inconsistencies in the data where one location contains data that is more recent than another location.

In another embodiment of the clinical data registry, the system links up with the national social security death index, and matches patients in clinical data registry database with patients listed in the national social security death index. If there is a discrepancy on the living status of a matched patient, the clinical data registry updates the patient record with the information obtained from the national social security death index.

The techniques described above can be implemented in digital electronic circuitry, or in computer hardware, firmware, software executing on a computer, or in combinations of them. The techniques can be implemented as a computer program product, i.e., a computer program tangibly embodied in tangible, machine-readable storage medium, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps of the techniques described herein can be performed by one or more programmable processors executing a computer program to perform functions described herein by operating on input data and generating output. Method steps can also be performed by, and apparatus of the invention can be implemented as, special purpose logic circuitry, e.g., an FPGA (field programmable gate array) or an ASIC (application-specific integrated circuit). Applications can refer to portions of the computer program and/or the processor/special circuitry that implements that functionality.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Storage media suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

A computing system implementing the invention can include clients and servers. A client and server are generally remote from each other and typically interact over a communication network. The relationship of client and server arises by virtue of computer programs running on the respective computers and having a client-server relationship to each other.

Having described various embodiments of the invention, it will now become apparent to one of skill in the art that other embodiments incorporating the concepts may be used. It is felt, therefore, that these embodiments should not be limited to the disclosed embodiments, but rather should be limited only by the spirit and scope of the following claims.

What is claimed is:

1. A method providing patient records in a registry database comprising:
   receiving, via a network, from a first site, a patient record, wherein the patient record was collected by the first site;
   storing, by a processor of a computing device, the patient record in one or more registry databases, wherein one or more registry databases store patient data from a plurality of sites according to a protocol specification, wherein the plurality of sites comprises the first site;
   determining, by the processor, that the first site is a member of one or more registry groups, wherein:
      each registry group of the one or more registry groups comprises two or more sites of the plurality of sites,
      each registry group of the one or more registry groups is granted access to at least a portion of patient data provided by the two or more sites, and
      the patient data comprises one or more patient records;
   associating, by the processor, the patient record with at least one of the one or more registry groups, wherein associating comprises making at least a portion of the patient record accessible to members of the at least one registry group;
   receiving, by the processor, a request for a report, wherein the request for the report is issued by a requesting site of the plurality of sites, and
      the request for the report identifies one or more search parameters, wherein the one or more search parameters include at least one member selected from the group consisting of: a) procedural information and b) one or more registry groups of which the requesting site is a member;
   determining, by the processor, patient data stored in the one or more registry databases satisfying the request; and
   providing, by the processor, to the requesting site, the patient data stored in the one or more databases satisfying the request.

2. The method of claim 1, comprising:
   receiving, by the processor, a request for patient data, wherein the request is associated with a second site different than the first site;
   determining, by the processor, the second site is a member of one or more of the at least one registry group; and
   providing, by the processor, to the second site, access to the patient data.

3. The method of claim 1, wherein the patient record includes at least one member selected from the group consisting of: patient medical condition information, pre-operative information, post-operative information, procedure type, operation information, anesthesia information, provider information, and hospital information.

4. The method of claim 1, wherein associating the patient record with the at least one registry group comprises:

identifying, by the processor, for each registry group of the at least one registry group, one or more fields of the patient record accessible to members of the respective registry group; and wherein the portion of the patient record accessible by members of each of the at least one registry group includes the one or more fields.

5. The method of claim 1, wherein a first registry group of the one or more registry groups comprises at least one of a vascular registry, an oncology registry, a national registry, and a regional registry.

6. The method of claim 1, wherein the search parameters include two or more registry groups of which the requesting site is a member.

7. The method of claim 1, wherein each site of the plurality of sites is a member selected from the group consisting of hospital, research facility, doctor's office, university, insurance company, medical company, and pharmaceutical company.

8. A system providing patient records in a registry database comprising:

one or more registry databases storing patient data from a plurality of sites according to a protocol specification, wherein the plurality of sites comprises at least the a site;

a processor;

a memory storing instructions thereon wherein the instructions, when executed, cause the processor to:

receive, via a network, from a first site, a patient record, wherein the patient record was collected by the first site;

store the patient record in the one or more registry databases;

determine that the first site is a member of one or more registry groups, wherein:

each registry group of the one or more registry groups comprises two or more sites of the plurality of sites, each registry group of the one or more registry groups is granted access to at least a portion of the patient data provided by two or more sites, and the patient data comprises one or more patient records; and associate the patient record with at least one of the one or more registry groups, wherein associating comprises making at least a portion of the patient record accessible to members of at least one registry group receive a request for a report, wherein the request for the report is issued by a requesting site of the plurality of sites, and the request for the report identifies one or more search parameters, wherein the one or more search parameters include at least one member selected from the group consisting of: a) procedural information and b) one or more registry groups of which the requesting site is a member;

determine patient data stored in the one or more registry databases satisfying the request; and provide, to the requesting site, the patient data stored in the one or more databases satisfying the request.

9. The system of claim 8, wherein the instructions, when executed, further cause the processor to:

receive a request for patient data, wherein the request is associated with a second site different than the first site;

determine, the second site is a member of one or more of the at least one registry group with which the patient data is associated; and provide to the second site, access to the patient data.

10. The system of claim 8, wherein the patient record includes at least one member selected from the group consisting of: patient medical condition information, pre-operative information, post-operative information, procedure type, operation information, anesthesia information, provider information, and hospital information.

11. The system of claim 8, wherein associating the patient record with the at least one registry group comprises:

identifying, by the processor, for each registry group of the at least one registry group, one or more fields of the patient record accessible to members of the respective registry group; and wherein the portion of the patient record accessible by members of each of the at least one registry group includes the one or more fields.

12. The system of claim 8, wherein a first registry group of the one or more registry groups comprises at least one of a vascular registry, an oncology registry, a national registry, and a regional registry.

13. The system of claim 8, wherein the search parameters include two or more registry groups of which the requesting site is a member.

14. The system of claim 8, wherein each site of the plurality of sites is a member selected from the group consisting of hospital, research facility, doctor's office, university, insurance company, medical company, and pharmaceutical company.

* * * * *